United States Patent [19]
Sayles

[11] Patent Number: 5,591,401
[45] Date of Patent: Jan. 7, 1997

[54] ONE-STEP TEST DEVICE

[76] Inventor: Philip W. Sayles, 172 Sycamore St., Watertown, Mass. 02172

[21] Appl. No.: 621,254

[22] Filed: Mar. 25, 1996

Related U.S. Application Data

[63] Continuation-in-part of Ser. No. 497,539, Jun. 30, 1995, Pat. No. 5,501,837, which is a continuation-in-part of Ser. No. 275,256, Jul. 15, 1994, Pat. No. 5,429,804.

[51] Int. Cl.$^6$ ................................................. G01N 21/01
[52] U.S. Cl. ............................ 422/58; 422/61; 422/100; 422/102; 436/165; 128/771; 604/404; 435/287.6; 435/287.7
[58] Field of Search .................... 422/58, 56, 61, 422/100, 102, 103; 436/165; 128/767, 771; 604/318, 404; 435/287.6, 287.7, 288.1

[56] References Cited

U.S. PATENT DOCUMENTS

| | | | |
|---|---|---|---|
| 4,690,801 | 9/1987 | Anderson | 435/287.6 |
| 4,865,813 | 9/1989 | Leon | 436/165 |
| 4,976,923 | 12/1990 | Lipsky et al. | 422/58 |
| 5,119,830 | 6/1992 | Davis | 128/771 |
| 5,283,038 | 2/1994 | Seymour | 435/287.6 |
| 5,403,551 | 4/1995 | Galloway et al. | 422/58 |

*Primary Examiner*—Jeffrey Snay
*Attorney, Agent, or Firm*—William Nitkin

[57] ABSTRACT

An improved test device for the testing of a fluid having a cup and a cover lid, such cover lid having a reagent test strip chamber containing a reagent test strip, a filling chamber, and a cutting chamber. An actuation cover with a window defined therein is positioned over the reagent test strip chamber, filling chamber and cutting chamber, such window positioned over the color change area of the reagent test strip. The actuation cover forms a fluid-tight seal around a first end of the reagent test strip which protrudes into the filling chamber. A pointed member is disposed under an actuation button in the cutting chamber. After the cup is filled with fluid and the cover lid is positioned thereon, the operator depresses the actuation button, forcing the pointed member through the floor of the cutting chamber to form an aperture therein. The test device is then inverted, allowing the fluid to pass through the thus formed aperture into the cutting chamber. When the test device is uprighted, the fluid passes into the bottom of the filling chamber and comes in contact with the protruding first end of the reagent test strip, such fluid to be drawn along the reagent test strip to accomplish the desired test to cause the appropriate color change to appear on such reagent test strip visible through the window in the actuation cover.

7 Claims, 2 Drawing Sheets

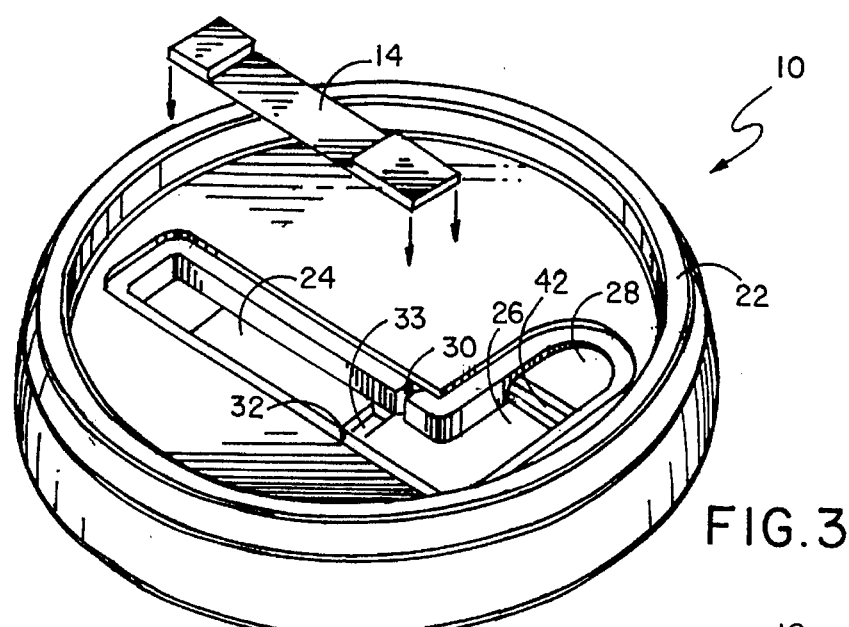
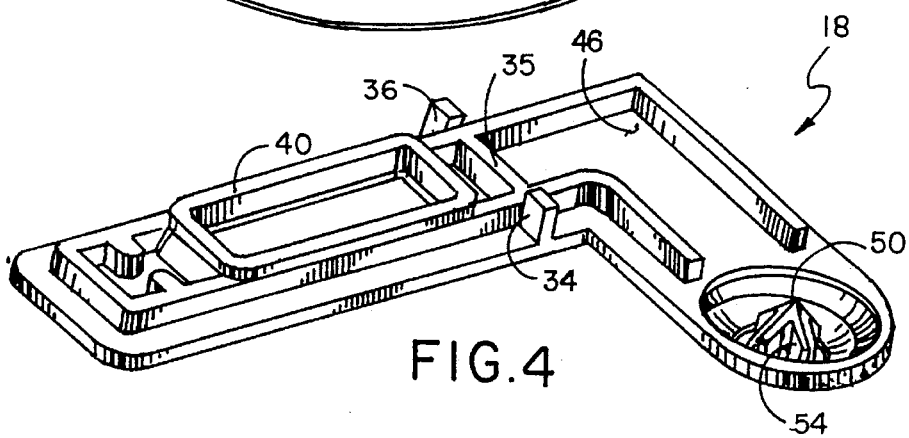
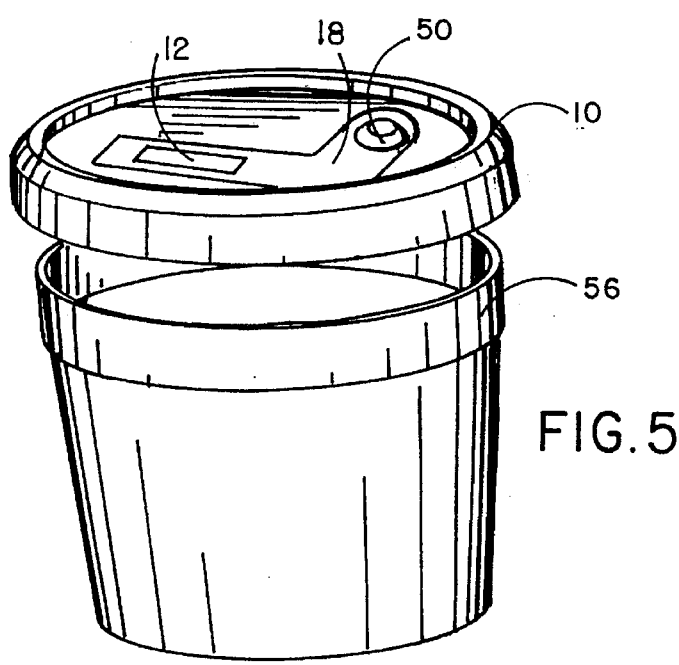

ONE-STEP TEST DEVICE

This application is a continuation-in-part of my previous application for a One-step Test Device, Ser. No. 08/497,539 filed Jun. 30, 1995, now U.S. Pat. No. 5,501,837, which was a continuation-in-part of my previous application for a One-step Testing Device, Ser. No. 08/275,256 filed Jul. 15, 1994, now U.S. Pat. No. 5,429,804.

BACKGROUND OF THE INVENTION

1. Field of the Invention

The device of this invention resides in the area of structures for the conducting of chromatographic immunoassay testing of a fluid on a reagent-containing membrane strip and more particularly relates to a test container holding the fluid to be tested to accomplish a test while the container is in a closed state.

2. Description of the Prior Art

Triage assay testing of bodily fluids is well known but has the serious disadvantage of requiring the tester to be exposed to contact with bodily fluids, such as urine, during the pipetting step. Such tests are slow, multi-step procedures which are difficult to carry out in hectic environments such as hospital emergency rooms.

In the prior art is U.S. Pat. No. 4,976,923 to Lipsky et al which patent discloses a specimen cup with a cover wherein the fluid to be tested is first placed in the specimen cup. The cover is positioned on the cup, and the closed cup is inverted so that the fluid can pass into apertures in the cover assembly where it reacts with a reagent therein to cause different color reactions which display the analytical characteristics of the fluid being tested. Such a specimen cup structure has great advantages in today's health environment where bodily fluids may contain dangerous viruses such as AIDS and the like. Health workers do not want to endanger their health by coming in direct physical contact with such fluids but still wish to perform necessary tests safely. In some cases the sealing of the fluids within such a specimen cup can be done by the person whose fluids are being tested. For example, in urine testing the subject whose urine is to be tested would urinate into the specimen cup and would then place the cover on the cup, sealing the urine in the cup. The lab technician performing the test need not open the cup or come in direct contact with the bodily fluids contained in the specimen cup. Thus a specimen cup which can be sealed during testing has a significant advantage over the open-cup fluid testing procedures of the past. U.S. Pat. No. 5,119,830 to Davis advances this concept in the prior art by providing a test space in the lid, under a transparent top, for positioning chemical test strip pads, such test space being initially sealed and when desired, a frangible portion of the inside of the lid can be broken open by pressure through the top of the lid to allow fluid to flood into the test space when the cup is inverted and cover the pads, the color change of which is visible through the transparent top of the test chamber.

SUMMARY OF THE INVENTION

It is a goal of this invention to provide an improved closed specimen cup testing system utilizing a cover lid containing a reagent membrane strip for the efficient conducting of chromatographic immunoassay testing. Chromatographic immunoassay strips cannot work if totally immersed in the fluid to be tested but must contact such fluid only at one end portion so that the fluid can be drawn along the strip by capillary action.

The structure of this invention in one embodiment provides for a cup, a cover lid, a reagent test strip chamber and a filling chamber disposed within the cover lid. A reagent test strip is positioned in the reagent test strip chamber. One end of the reagent test strip extends through an opening formed by the lid and the activation cover and the other end protrudes into a filling chamber where such reagent test strip's protruding end can come into contact with the fluid to be tested while at the same time preventing such fluid from contacting or flooding over the balance of such strip. After the inside of the lid is punctuated, as described below, and the cup is inverted, the fluid to be tested passes through the aperture thus formed into, and filling, the filling chamber with a specific amount of fluid. The cup is then uprighted, and the fluid of a specific amount pools in the filling chamber and contacts only the protruding end of the reagent test strip. The fluid is then drawn along the reagent test strip to the color change area. The visible color change area of the reagent test strip is visible through an elongated open window formed in the actuation cover.

In use, when the fluid specimen is placed within the specimen cup and the cover lid is affixed in fluid-tight relationship thereon such as by screw threads or other attachment means, the filling chamber is opened to the inside of the cup, as more fully described below, and the specimen cup is inverted, allowing a predetermined amount of the fluid to be tested to enter the filling chamber through the aperture. When the cup is uprighted, the fluid falls to the bottom of the filling chamber where it pools and comes in contact with the exposed, protruding first end of the reagent test strip which extends out of the opening in the reagent test strip chamber. The fluid is drawn along the reagent test strip toward the center of the reagent test strip chamber by capillary action until the fluid comes to the bands of the chromatographic Immunoassay test reagent where a color change can occur to perform the desired test. Very small amounts of the fluid sample are carried by such capillary action from the filling chamber along the length of the reagent test strip. An opening forming a window in the actuation cover on the top of the cover lid disposed immediately above the reagent test strip allows the visible color change area of the reagent test strip to be observed for color change reactions, and a label or indicia adjacent to such open window can identify the test such reagent test strip is performing. The testing device of this invention combines all the advantages of a closed container test system for fluids, such as urine and the like, and provides for a uniform measured quantity of fluid to be positioned at the protruding end of the reagent test strip.

BRIEF DESCRIPTION OF THE DRAWINGS

FIG. 3 illustrates a perspective view of the cover lid with the actuation cover removed, showing the reagent test strip chamber and filling chamber.

FIG. 4 illustrates a perspective bottom view of the actuation cover.

FIG. 5 illustrates a perspective view of the cover lid disposed above a cup having fluid therein.

DESCRIPTION OF THE PREFERRED EMBODIMENT(S)

Figure 1:
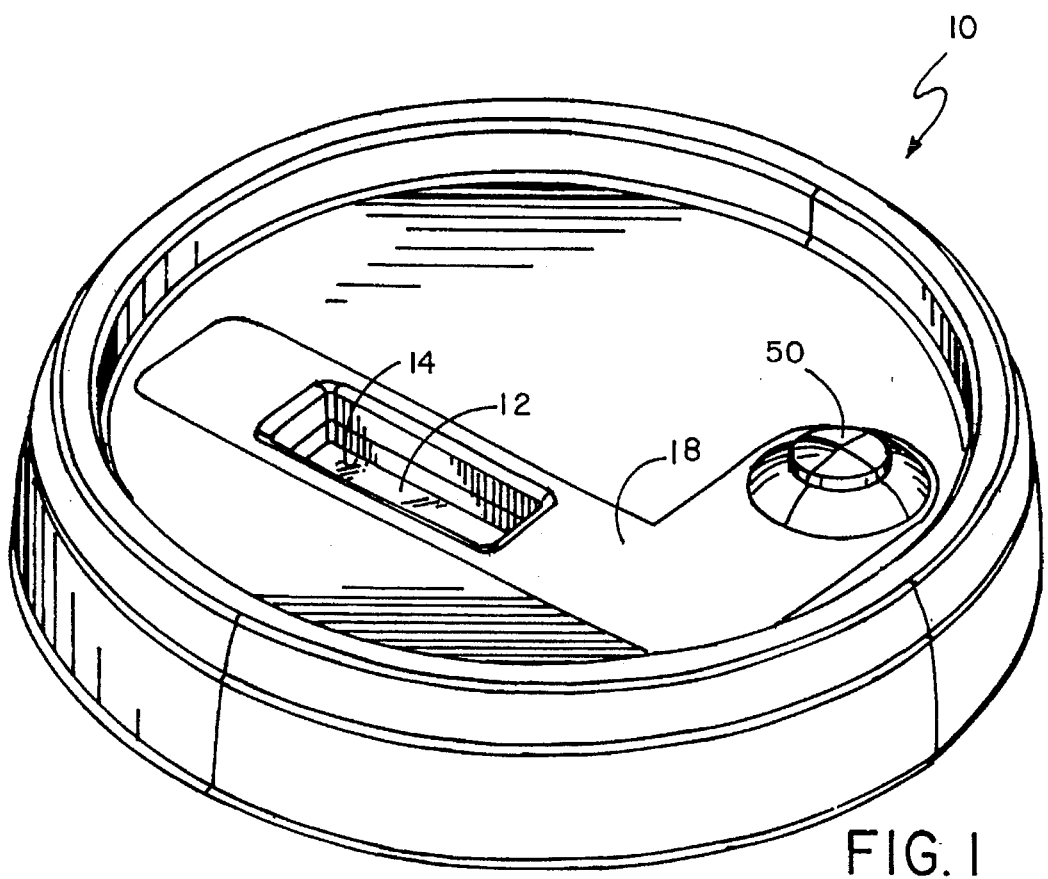
FIG. 1 illustrates a perspective view of one embodiment of the cover lid of this invention.

FIG. 1 illustrates cover lid 10 having a top and bottom of the fluid testing device of this invention. Not shown in this view is the cup containing the fluid to be tested which cup is well known. In use of the device of this invention the fluid to be tested is deposited in such cup. The cover lid can be attached to the cup by screw-on threads disposed at the outer top surface of the cup which threads would interengage in fluid-tight relationship with mating threads disposed on the inner side of the cover lid side wall. Other means of fluid-tight attachment of the cover lid to the cup, such as snap-on friction-fit, can also be used as long as such means securely hold the cover lid onto the cup when the testing device is inverted for the fluid to enter the filling chamber, as described below. In actuation cover 18, as best seen in FIG. 4, on cover lid 10 is defined open window 12 immediately above the visible color change area of reagent test strip 14. Indicia 16 can be printed on the cover lid's top surface to indicate the particular test being performed on the reagent test strip. L-shaped actuation cover 18 is permanently affixed to the top of cover lid 10 and has test actuation button 20 thereon. Cover lid 10 can be formed of a plastic molded lower lid 22 onto which can be permanently affixed plastic actuation cover 18.

Figure 2:
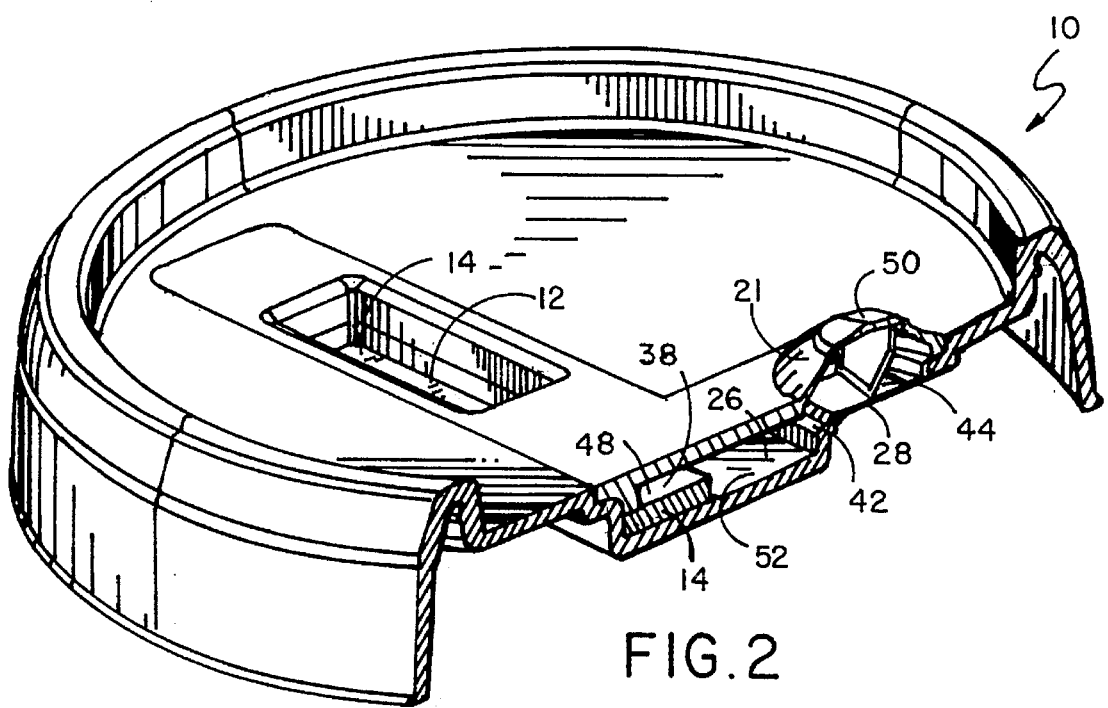
FIG. 2 illustrates a perspective cutaway view of a portion of the cover lid showing a reagent test strip extending from the strip chamber into the filling chamber.

FIG. 3 illustrates a perspective view of lower lid 22. Several chambers can be formed in the top thereof during its molding process. Reagent test strip chamber 24 can be formed to receive reagent test strip 14 seen disposed thereabove, the first end of which is seen in FIG. 2 protruding into filling chamber 26. Reagent strip chamber 24 extends to filling chamber 26 which has a portion of its bottom forming a thin-walled elevated piercing area 28 that can be pierced as described below, creating an aperture therein. Filling chamber 26 is spaced at approximately a 90-degree angle to reagent test strip chamber forming an L shape. When reagent test strip 14 is positioned in reagent test strip chamber 24, its first end 38 extends beyond first and second rib receipt openings 30 and 32 on each side thereof into filling chamber 26. As seen in FIG. 4 which is a bottom view of actuation cover 18, first rib member 34 and second rib member 36 are positioned to mate into first and second rib receipt openings 30 and 32, respectively, to form a seal around protruding first end 38 of reagent test strip 14 with upper rib member 35 on actuation cover 18 to form a fluid-tight seal with the base of the reagent test strip chamber around the reagent test strip, the protruding end 38 of which is seen in the cutaway view of FIG. 2 extending into filling chamber 26. A depression 33 can be provided in the floor of reagent test strip chamber 24 to form a "gate" to prevent the capillary action from occurring too quickly with fluid drawn between the reagent test strip chamber floor and the reagent test strip. The use of such a "gate" is known in the art to be helpful when using reagent test strips which rest on surfaces. As can be seen in FIG. 4, bottom 40 of the area of actuation cover 18 forms a window, the sides of which extend inward to contact, and help retain, the reagent test strip in place, such window being disposed directly above the color change area to be viewed on the reagent test strip. The structures of the actuation cover and cover lid interact to retain the reagent test strip in an area that cannot be contacted by fluid except for first end 38 of reagent test strip 14 which extends into filling chamber 26 and prevent any fluid from escaping to the outer environment through window 12. Actuation cover 18 can be permanently held in place on lower lid 22 by gluing, ultrasonic welding or equivalent means. Part of the actuation cover is pointed member 50 which is disposed inside the bottom of button 20. When button 20 which has flexible sides 21 is depressed, pointed member 50 is moved downward and pierces through the thin wall of elevated piercing area 28 of the cutting chamber floor which is elevated from bottom 52 of filling chamber 26 at a height generally parallel to top 48 of the reagent test strip seen in FIG. 2. The cover lid has step-down area 42 extending from such elevated piercing area 28 down to filling chamber 26 such that when the test device is inverted after pointed member 50 has punctured through elevated piercing area 28 of cutting chamber 44 and the pointed member has been pulled back out of such aperture by the resilience of the sides of actuation button, the fluid will pass into and fill cutting chamber 44 as well as the inside 46 of the filling chamber on the inside of actuation cover 18 substantially up to the top 48 of reagent test strip 14. The sides of first end 38 would still be uncontacted by the fluid coming into filling chamber 26. In other embodiments the pointed member can have rib members 54 extending therearound which, after pointed member 50 has pierced piercing area 28, allow the fluid to pass thereby without the need to withdraw the pointed member from piercing area 28, which openings between such rib members 54 allow fluid to pass through such formed spaces between such rib members 54 and the perimeter of the aperture. Once the area of the cutting chamber and parts of the filling chamber are filled with a specific amount of fluid, the test device is uprighted. The fluid then falls downward and pools in the bottom of filling chamber 26, some passing from cutting chamber 44 down step-down area 42 and also flowing down from the top of reagent test strip 14 to fill the filling chamber to generally the height of first end 38 of reagent test strip 14 so that the fluid can then be drawn by capillary action along reagent test strip 14 to the area under test window 12 so that the results can be observed. FIG. 5 illustrates such a cover lid 10 disposed above cup 56.

Although the present invention has been described with reference to particular embodiments, it will be apparent to those skilled in the art that variations and modifications can be substituted therefor without departing from the principles and spirit of the invention.

I claim:

1. An one-step test device having a test mode, said device having a cup for receipt of a fluid specimen to be tested and a cover lid above to be attached to said cup in a fluid-tight relationship, further comprising:

said cover lid having a top and a bottom, said cover lid having defined in said top thereof a reagent test strip chamber having a floor and first and second sides formed from said cover lid and a filling chamber having a floor formed from said cover lid, said reagent test strip chamber and said filling chamber in communication with one another;

a reagent test strip positioned in said reagent test strip chamber having a first end, a second end and a color change testing area disposed between said first and second ends;

an actuation cover having a top and a bottom, said actuation cover covering both said reagent test strip chamber and said filling chamber;

means to prevent said fluid from passing from said filling chamber into said reagent test strip chamber, said means providing for said first end of said reagent test strip to extend from said reagent test strip chamber protruding into said filling chamber;

a cutting chamber defined in said cover lid, said cutting chamber having a floor formed from said cover lid and being in fluid communication with said filling chamber;

means disposed on said bottom of said actuation cover, when activated, to pierce said floor of said cutting chamber, causing an aperture to be formed therein extending through said floor of said cutting chamber;

said cover lid when positioned on said fluid-filled cup and after said means to pierce said cutting chamber floor has been activated making an aperture therein, allowing fluid, when said test device is inverted, into said cutting chamber through said thus-formed aperture, said test device, when uprighted, allowing said fluid to drain from said cutting chamber and to pool in said filling chamber to come in contact with said first end of said reagent test strip to cause said fluid to be carried along said reagent test strip to said color change testing area; and an open window defined in said actuation cover, said window disposed above said color change testing area, through which window the test results can be viewed.

2. The test device of claim 1 wherein said means to prevent fluid from passing from said filling chamber into said reagent test strip chamber comprises:

first and second slots defined, respectively, in said first and second sides of said reagent test strip chamber; and first and second rib members disposed at said bottom of said actuation cover, said first and second rib members positioned to mate, respectively, into said first and second slots to surround said reagent test strip in a fluid-tight relationship, allowing said first end of said reagent test strip to be positioned in said filling chamber.

3. The test device of claim 2 wherein said means disposed on said actuation cover to pierce said floor of said cutting chamber comprises a pointed member, said actuation cover extending upwards to form a collapsible button above said pointed member whereby when said actuation button is manually depressed, said pointed member is driven through said floor of said cutting chamber.

4. The test device of claim 3 wherein said window defined in said actuation cover further includes:

downwardly extending side walls in said actuation cover around said window, such side walls to sandwich said reagent test strip between said sides and the floor of said reagent test strip chamber and help retain said reagent test strip in said reagent test strip chamber.

5. The test device of claim 4 wherein said filling chamber is disposed at a right angle to said reagent test strip chamber and said actuation cover is formed in an L shape, said actuation cover being permanently affixed to said cover lid above said reagent test strip chamber, said filling chamber and said cutting chamber.

6. The test device of claim 5 wherein said cutting chamber floor is elevated toward said top of said cover lid from the floor of said filling chamber, said test device further including a step down area defined in said cover lid between said elevated cutting chamber floor and said floor of said filling chamber.

7. The test device of claim 6 wherein said cutting chamber and filling chamber receive therein a predetermined amount of said fluid to be tested such that when said test device is inverted and then uprighted, the test device contains sufficient fluid in said filling chamber to allow said protruding first end of said reagent test strip to absorb sufficient fluid to be carried by said reagent test strip to said color change area and said means to prevent fluid from otherwise passing from said filling chamber into said reagent test strip chamber prevents any excess fluid from escaping from said filling chamber through said reagent test strip chamber and out said open window into the outer environment around said test device.

* * * * *